United States Patent
Savage

[11] Patent Number: 6,040,150
[45] Date of Patent: Mar. 21, 2000

[54] FORMULATIONS FOR FLUOROGENIC PEROXIDASE ASSAYS

[75] Inventor: M. Dean Savage, Rockford, Ill.

[73] Assignee: Pierce Chemical Company, Rockford, Ill.

[21] Appl. No.: 09/206,878

[22] Filed: Dec. 8, 1998

[51] Int. Cl.[7] .............................. C12Q 1/28; C12Q 1/00; G01N 33/53; G01N 21/76

[52] U.S. Cl. ................................ 435/28; 435/4; 435/7.1; 436/172

[58] Field of Search ................... 435/28, 4, 7.1; 436/172, 800, 501

[56] References Cited

U.S. PATENT DOCUMENTS 4,152,411  5/1979  Schall, Jr. .................................. 424/1
5,543,332  8/1996  Lihme et al. ............................ 436/528

FOREIGN PATENT DOCUMENTS 4-234998  12/1990  Japan.

OTHER PUBLICATIONS

Zaitsu et al. Analytical Biochemistry 109:109–113, 1980.

Primary Examiner—Bradley L. Sisson
Assistant Examiner—Devesh Srivastava

[57] ABSTRACT

An improved method is disclosed for assaying peroxidase or peroxide activity utilizing a substrate solution containing a fluorogenic phenolic compound, hydrogen peroxide and a metal chelating compound. The improvement inclosed including within the assay, in an amount sufficient to enhance the effective working range of the assay, a boron acid or salt thereof, or a phosphine-based or hydride-based reducing agent.

5 Claims, 4 Drawing Sheets

FORMULATIONS FOR FLUOROGENIC PEROXIDASE ASSAYS

FIELD OF THE INVENTION

The present invention relates to the fluorometric assay of peroxidase activity and, more particularly to improvements in such an assay.

BACKGROUND OF THE INVENTION

Zaitsu and Ohkura, Analytical Biochemistry, 109, 109–113 (1980) describe the use of phenolic compounds as fluorogenic substrates for the horseradish-peroxidase (HRP)-mediated reaction with hydrogen peroxide in order to assay for peroxidase activity or the peroxide. Of the fluorogenic substrates, 3-(p-hydroxyphenyl)propionic acid (HPPA) was identified as being preferred in providing a rapid and sensitive assay. Tuuminen, et al., Journal of Immunoassay, 12(1), 29–46 (1991) recognized the observations of Zaitsu and Ohkura and applied the use of HPPA as a fluorogenic substrate of labelled HRP in an immunoassay.

A limitation accompanying the use of HPPA as a fluorogenic substrate for peroxidases used as labelling enzymes in enzyme immunoassay methods was recognized in Japanese Patent Application No. 4-234998 filed on Dec. 27, 1990, by Kohusai Shiyaku K. K. It was observed that peroxidase-mediated enzyme immunoassay methods using HPPA were intrinsically highly sensitive, but that HPPA formulated in buffers to provide the substrate solution undergoes condensation as a result of the presence of metal ions and is converted into a fluorescent substance which results in a rise in the reagent blank, thus decreasing sensitivity and measurement precision. The Japanese patent application discloses that a chelating agent such as an aminopolycarboxylic acid or aminopolyphosphonic acid, or salts thereof, can be used to stabilize formulated HPPA substrate solutions by reducing the rise in the reagent blank.

While demonstrating an improvement in the assay, following the technique illustrated in the Japanese application and other cited literature does not provide for an optimum assay. There is still room for improvement in enhancing the sensitivity of the assay and, in particular, in enhancing its utility by extending the effective working range of the assay by broadening the effective peroxidase reaction response curve, as defined by peroxidase concentration, time, or temperature. With conventional substrates containing a fluorogenic phenolic compound, hydrogen peroxide, and, preferably a metal chelator, there is a heretofor unrecognized limitation on these substrates that restricts their effective working range. The limitation is the formation of certain nonproductive product(s) during the course of the reaction of the substrate solution with peroxidase along with the productive formation of the fluorescent product of the reaction. The nonproductive product(s) possess optical characteristics interfering with the quantitative measurement of fluorescence generated by peroxidase activity. These nonproductive product(s) absorb light within the phenolic compound's fluorescent product excitation/emission spectra. Accordingly, the fluorescence measured is less than that which the reaction generates, the difference being that absorbed by nonproductive product(s).

Having the above in mind, the presence of the nonproductive product(s) limits the effective working range of available fluorogenic phenolic substrates for determining peroxidase activity. In the assays, there is a point, either determined by reaction time, or peroxidase concentration, or temperature, where the concentration of nonproductive products(s) increases to a critical point where the continued rise in fluorescence is defeated, and indeed the fluorescence may be observed to decrease, thus disabling the ability to distinguish peroxidase concentrations or reaction times from dissimilar values. In other words, due to the presence of the nonproductive product(s), the measured fluorescence at one concentration is depressed to the same as the measured fluorescence at a lower concentration or the measured fluorescence is depressed to the same as the measured fluorescence at lower times during the reaction. Therefore, it would be desirable to either fashion a formulation so that this critical point can be manipulated within an assay to increase effective working range, or to increase effective working range by providing means for minimization of the consequences of the critical point by eliminating the nonproductive product(s).

SUMMARY OF THE INVENTION

Now in accordance with the present invention, there is provided means for influencing the presence of nonproductive product(s) formed during the peroxidase-mediated reaction with a substrate solution containing a fluorogenic phenolic compound with hydrogen peroxide. And in turn, the critical point within an assay can be manipulated or minimized with respect to its consequences. In accordance with the present invention, there is provided an improvement in the general method of assaying for peroxidase or peroxide which involves reacting a substrate solution containing a fluorogenic phenolic compound with peroxidase in the presence of hydrogen peroxide in a substrate buffer formulation and measuring the resulting fluorescence intensity. The improvement provided by the present invention centers on including in the assay, in an amount sufficient to enhance the effective working range of the assay, a boron acid or salt thereof, or a phosphine-based or hydride-based reducing agent. In conventional practice, the concentration of peroxidase or peroxide is quantified by comparing the measured fluorescence intensity with that generated by a standard curve.

In practicing the improvement of the present invention involving the inclusion of the boron acid, such can be included in the formulated substrate solution, which can be subsequently be used in either stopped, nonstopped, or kinetic assay formats. In practicing the improvement of the present invention involving the inclusion of the reducing agent, this finds utility in stopped assay formats and the reducing agent can be included directly in the enzymatic stop solution.

Including either the boron acid and/or the reducing agent in the assay serve to enhance the effective working range of the assays by controlling or minimizing the formation of the nonproductive product(s) during the course of the peroxidase reaction with the fluorogenic phenolic substrate solution and/or minimizing the presence of such nonproductive product(s) at the end of the assay.

DESCRIPTION OF THE INVENTION

Figure 1:
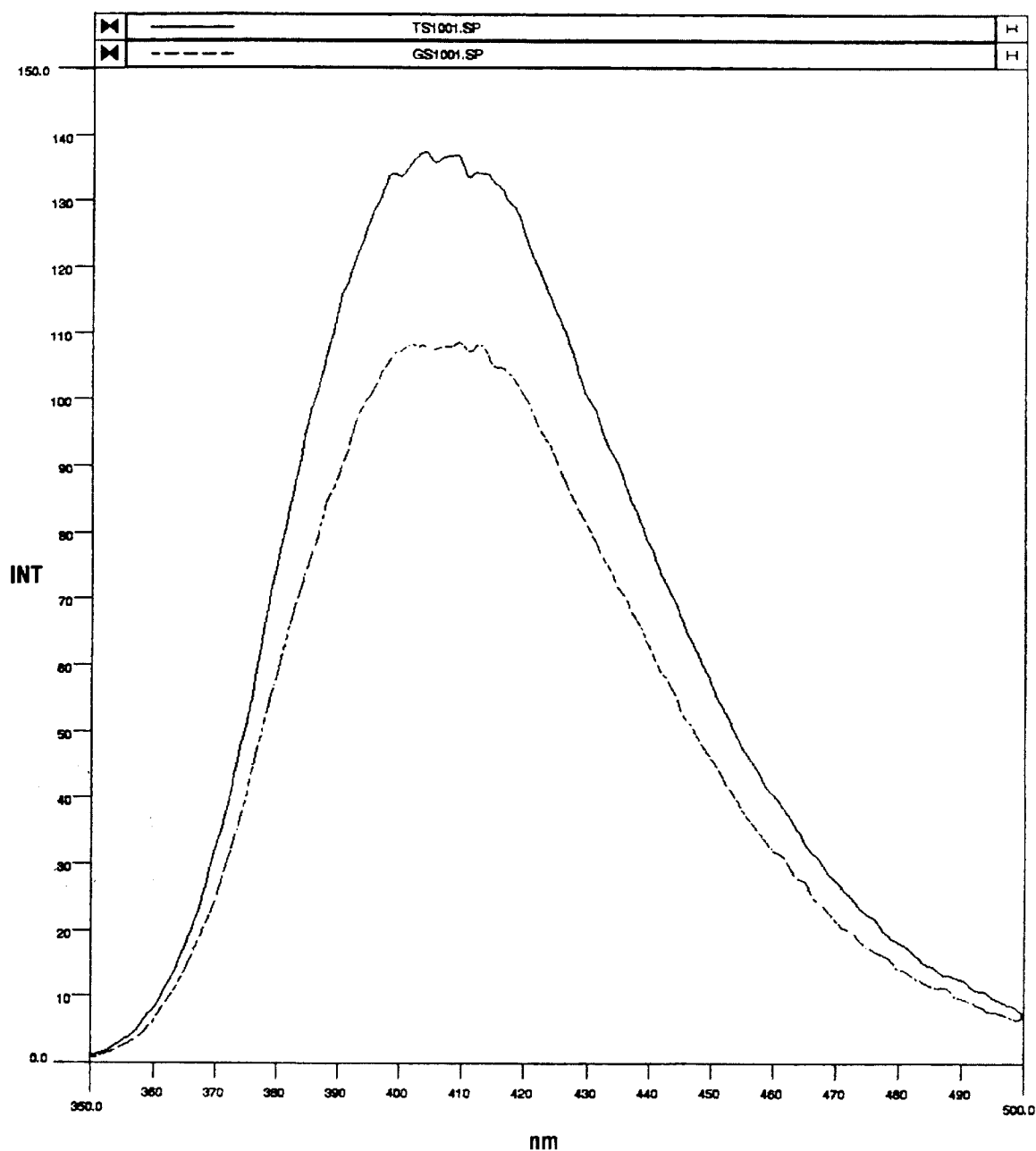
FIG. 1 illustrates the relative fluorescent intensity of a peroxidase-reacted HPPA working substrate solution stopped after 30 minutes reaction time by the addition of an alkaline solution either with (solid line) or without (broken line) the presence of the reducing agent, tris(2-carboxylethyl)phosphine hydrochloride (TCEP).

The improvements described herein are applicable with respect to those general methods of assaying for peroxide or peroxidase activity or concentration based on the use of fluorogenic phenolic compounds contained in substrate formulations including hydrogen peroxide and preferably a metal chelating agent(s). Useful phenolic comounds compounds have have been identified in the literature such as in the above identified Zaitsu and Ohkura publication. Particularly useful are those p-hydroxyphenyl compounds identified therein with a substituent having 2 or 3 methylene groups, without a 3-methoxy group. 3-(4-hydroxyphenyl) propionic acid (HPPA) and p-tyrosol are identified as particularly preferred with horseradish peroxidase as the enzyme.

Concerning the metal chelating agent, preferably these chelating agents contain three or more alkylene carboxylic acid groups or alkylene phosphonic acid groups bonded to nitrogen. While ethylenediamine tetraacetic acid (EDTA) in the form of its disodium salt, is preferred, other particularly useful chelating agents of this type are identified in the above referenced Japanese application. As to hydrogen peroxide, such can be supplied in the form of hydrogen peroxide, or generated in situ by compounds evolving hydrogen peroxide, such as sodium perborate.

Useful substrate solutions generally contain the fluorogenic phenolic compound in an aqueous buffer. The phenolic compound and hydrogen peroxide are usually present in concentrations sufficient to saturate the enzyme. Where metal chelating additives are included, concentration ranges of 0.001 mM to 100 mM are useful.

Assays for peroxidase activity are run either in a stopped or nonstopped format. In a stopped format, the peroxidase activity is intentionally terminated at some time during the course of the reaction by addition of a stop solution with subsequent fluorescence measurement. Typically, stop solutions are buffered alkaline formulations based on glycine, where activity is terminated by pH modification, or can be based on formulations relying upon peroxide destruction for activity termination, such as sodium thiosulfate. Nonstopped formats do not rely on the addition of a stop solution, but instead are based on fluorescence determination at a given time point within the course of the peroxidase reaction or between two time intervals within the course of the peroxidase reaction.

In keeping with the present invention, the effective working range of the assay can be improved by including in the assay, a boron acid, or salt thereof or a phosphine-based or hydride-based reducing agent. Examples of useful boron acids are borate and perborate and salts thereof. Boric acid and sodium perborate are particularly preferred for use in practicing the present invention. In practicing this aspect of the invention, hydrogen peroxide is also provided to the substrate formulation as a natural course of chemical equilibrium, and the benefits of this invention are practiced once the amount of hydrogen peroxide exceeds that required to saturate the enzyme. To realize the advantages associated with the inclusion of boron acid, or salt therefore, in enhancing the effective working range, the acid or salt are included in the substrate solution in an amount of at least 1 mM and preferably at least 2 mM up to a maximum of about 50 mM.

The use of a boron acid, or salt thereof, as above described is applicable to both a stopped and nonstopped format. As a matter of course, the preferred assay format is individual to a given assays requirement, and other factors such as instrumentation. In further keeping with that aspect of the present invention involving the use of the reducing agent to enhance the effective working agent, the applicability resides within a stopped assay format since the reagents themselves consume peroxide and stop the reaction. However, both the boron acid and reducing agent can be used within the same stopped assay.

Turning to the use of a reducing agent, as described in the present invention, as a class, hydride-based or phosphine-based reducing agents are useful. Partcularly preferred are sodium borohydride and tris(2-carboxylethyl)phosphine hydrochloride (TCEP), both being water-soluble reagents. It is preferable to use the reducing agent in excess molar quantities over the amount of peroxide used in the assay, and preferably at two to three times the molar quantity of peroxide used in the assay.

EXAMPLE I

This examples illustrates the improved fluorescence intensity effected by the inclusion of TCEP in the stop solution used for a peroxidase HPPA substrate reaction. In this example, 25 ng (0.5 µl of a 1 to 100 dilution in 0.2 M Tris, pH 8.0) of biotinylated HRP (stock concentration=5 mg/ml) was added to 4 ml of formulated HPPA working substrate solution (prepared by mixing nine volumes of 22 mM HPPA, 0.2 M Tris, pH 2 mM disodium EDTA, pH 8.0 to one volume 0.1 M sodium acetate, 2 mM disodium EDTA, 3.07 g sodium perborate/liter, pH 5.0) and allowed to react for 30 minutes at room temperature. This solution was then split between two clear acrylic fluorometer cuvettes (1 cm pathlength) as two 1.5 ml aliquots and each aliquot was then stopped by addition of 1.5 ml 0.2 M glycine, pH 10.5 or 1.5 ml 0.2 M glycine, 2.7 g TCEP/liter, pH 10.5. Fluorescence spectra was then determined using a Perkin-LS50 fluorometer using 320 nm excitation, 2.5 nm slit widths, with PMT voltage set at 900 mV.

As shown in FIG. 1, the addition of the reducing agent, TCEP increases the fluorescent intensity of the phenolic compound's fluorogenic product by elimination of the interfering absorbance characteristics of the nonproductive product(s) produced during the reaction with peroxidase. Accordingly, the fluorescent intensity is increased on the order of approximately 27%, thereby extending the effective working range of the assay by that amount, whether defined as a function of concentration or time.

EXAMPLE II

This example illustrates the use of the reducing agent, sodium borohydride, as a reagent to enhance the fluorescence intensity in order to elevate the critical point of an assay and expand the effective working range of an assay. Biotinylated HRP diluted in PBS (0.1 M sodium phosphate, 150 mM NaCl, pH 7.4) was bound at 100 µl per well to a Neutravidin coated white microtiter plate at varying concentrations of 0–75 ng/ml, the 75 ng/ml concentration being selected to exceed the maximum for binding of biotinylated HRP onto the coated plate surface, for 1 hour at room temperature with mild shaking followed by 3×200 µl washes with PBS. The plate then received 100 µl of HPPA working substrate (prepared by adding 4.5 ml 22 mM HPPA, 2 mM disodium EDTA, 0.1 M Tris, pH 8.1 to 0.5 ml 20 mM sodium perborate, 2 mM disodium EDTA, 0.1 M sodium acetate, pH 5.0) solution and the reaction was allowed to proceed for 30 minutes at room temperature followed by addition of 100 µl of stop solution (1.5 M glycine, pH 10.5). Thus, previously reacted and stopped HPPA working solutions were then pooled for each separate biotinylated HRP concentration and transferred at 200 µl per well into a separate clean opaque white CoStar microtiter plate to arrive at 12 homogenous peroxidase dilution series. Either 20 µl of 100 mM sodium borohydride in 1.5 M glycine, pH 10.5, or 20 µl of 1.5 M glycine, pH 10.5, were then pipetted into each dilution series and the fluorescence was measured after 18 minutes of incubation at room temperature using a Perkin-Elmer LS50 fluorometer using 325/420 nm excitation/emission wavelengths with 4.5/10 nm slit width settings and PMT voltage set at 900 mV.

Figure 2:
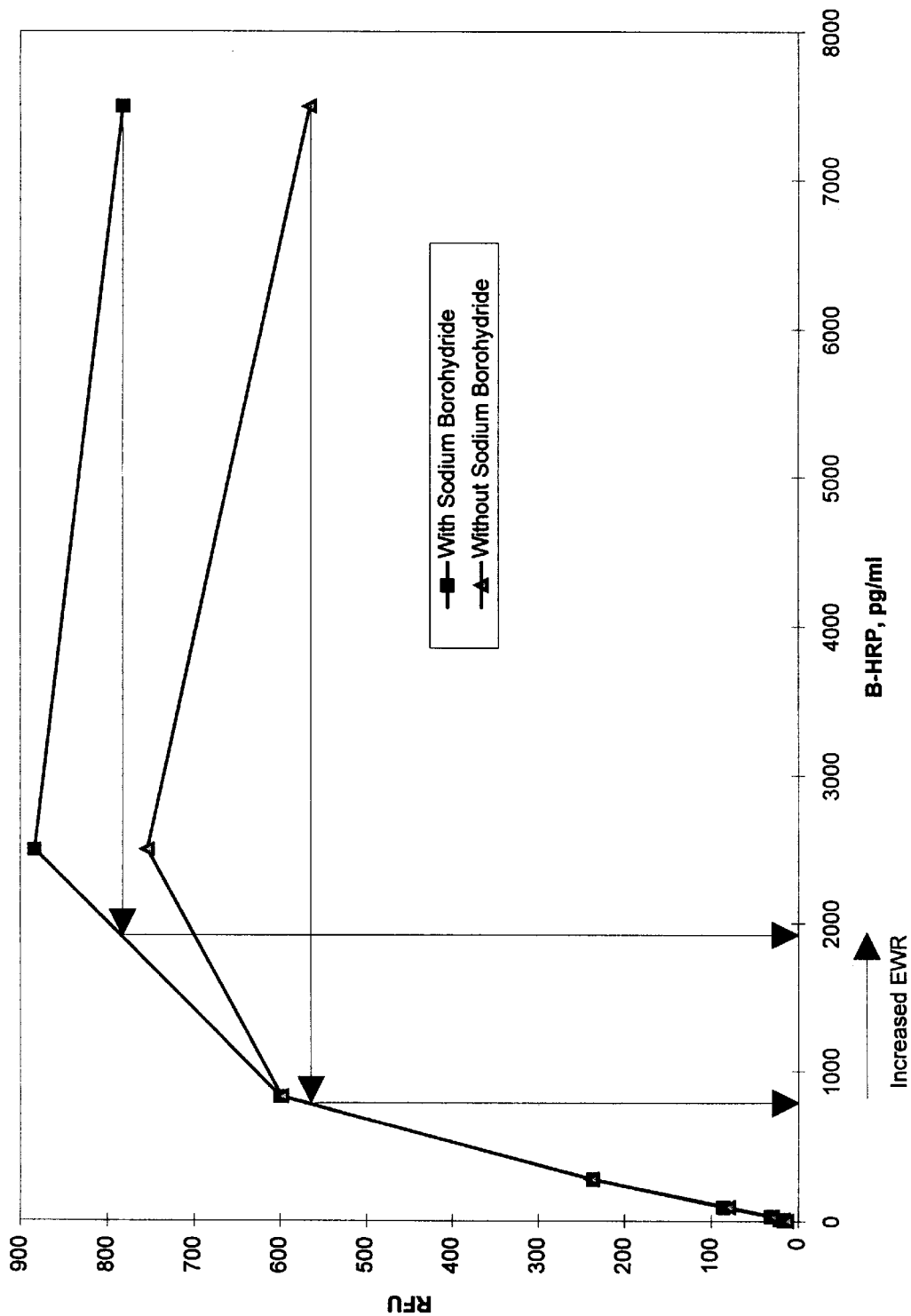
FIG. 2 illustrates the relative fluorescence of a peroxidase-reacted HPPA working substrate solution previously stopped with alkaline pH buffer either with or without addition of 75 mM sodium borohydride.

The measured fluorescence intensity is shown in FIG. 2. As shown, fluorescence intensity increases as sodium borohydride increases and accordingly, the effective working range (EWR) of the assay, as a function of peroxidase concentration increases. In particular, as shown in the figure, the working range of the assay employing no added borohydride exhibited an effective working range of 0–8 ng/ml whereas the assay employing borohydride exhibited an effective working range of 0–18 ng/ml.

EXAMPLE III

This example illustrates the relative fluorescence of a peroxidase-reacted HPPA working substrate solution as a function of time in a non-stopped reaction format. In this example, 50 ng (1 µl of a 1 to 100 dilution in 0.2 M Tris, pH 8.0) of biotinylated HRP (stock concentration=5 mg/ml) was added to 4 ml of formulated HPPA working solution (prepared by mixing nine volumes of 22 mM HPPA, 0.2 M Tris, pH 2 mM disodium EDTA, pH 8.0 to one volume 0.1 M sodium acetate, 2 mM disodium EDTA, 3.07 g sodium perborate/liter, pH 5.0) and the resultant fluorescent spectra between 350 and 500 nm was followed over time by repeated measurements at the following nine time intervals, in seconds: 1=40, 2=105, 3=210, 4=285, 5=425, 6=515, 7=825, 8=1068, and 9=1220 seconds. Fluoroescence spectra was obtained using a Perkin-LS50 fluorometer using 320 nm excitation, 2.5 nm slit widths, with PMT voltage set at 900 mV.

Figure 3:
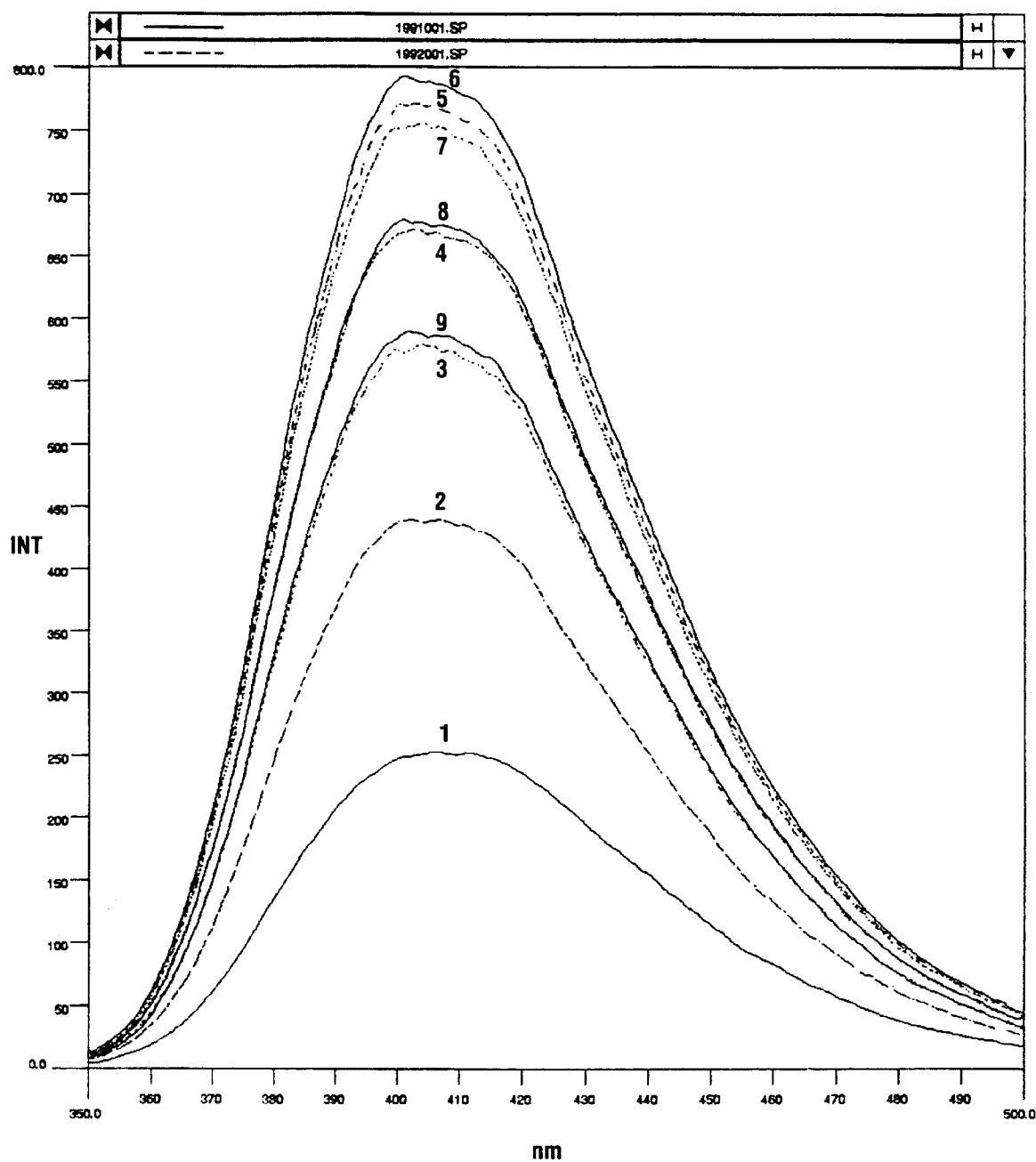
FIG. 3 illustrates the relative fluorescence of a peroxidase-reacted HPPA working substrate solution as a function of time in a non-stopped reaction format.

As can be seen in FIG. 3, observed fluorescent intensity increases as a function of time until a point is reached where the interfering nonproductive product(s) concentration reaches a critical point at 515 seconds (number 6) where observed fluorescent intensity is reduced to a point corresponding to the equivalent fluorescent intensity at a shorter reaction time. Accordingly, once that point is reached, the working range, as a function of time, of the assay is exceeded, i.e. as reaction time increases beyond that point, the effective working range defined in this context as time is further reduced from a maximum of 0–515 seconds to a minimum of 0–210 seconds. As is evident, by reference to FIG. 1, the placement of the critical point in FIG. 1 can be increased by stopping the reaction with TCEP. Accordingly, were the reaction to be stopped with TCEP after the aforementioned critical point (number 6) is reached, the effective working range can be extended for the assay.

EXAMPLE IV

Figure 4:
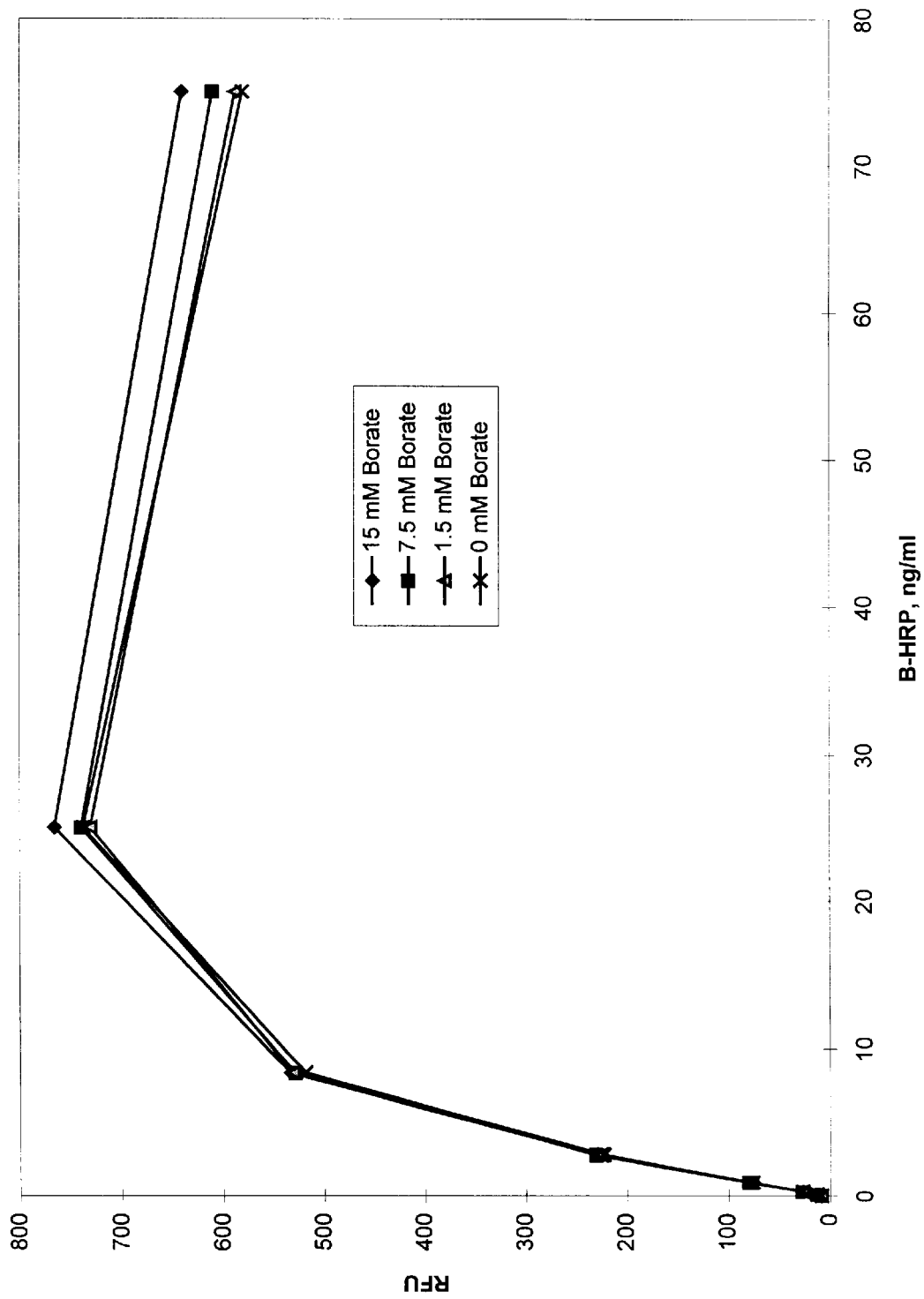
FIG. 4 illustrates the relative fluorescence of peroxidase-reacted HPPA working substrate solution in a stopped assay format as a function of varying boron acid concentration as supplied by borate ion.

FIG. 4 illustrates the relative fluorescence of peroxidase-reacted HPPA working substrate solution in a stopped assay format at as a function of varying boron acid concentration as supplied by borate ion. To a Neutravidin Coated white microtiter plate bound with biotinylated HRP as previously described, was added 100 µl of HPPA working solution prepared with varying concentrations of borate. These working solutions were prepared by adding 58 µl of 120 mM sodium perborate, 0.1 M sodium acetate, pH 5.0 to 1.74 ml of 22 mM HPPA, 2 mM disodium EDTA, 0.1 M Tris, pH 8.1, and either 0, 0.02, 0.1, or 0.2 ml 150 mM boric acid, pH 8.1, with final adjustment to 2 ml volume with MilliQ water to arrive at a borate concentration series of 0, 1.5, 7.5, and 15 mM in the formulated HPPA working solutions. Reaction proceed for 50 minutes at room temperature at which time, the plate was read in the non-stopped assay mode on a Perkin-Elmer LS50 fluorometer using 320/420 nm excitation/emission wavelengths with 10/4.2 nm slit widths and PMT voltage set to 900 mV. After reading, the plate was allowed to continue to react for additional time until the two highest concentration series began to show visible discoloration. This point was reached at 75 minutes total incubation time and the reaction was then stopped by addition of 100 µl of 0.75 M glycine, pH 10.3, and the plate was then read again using the same instrumentation and settings.

As illustrated in FIG. 4, as boron acid concentration is increased, once a threshold amount of peroxidase is present, the fluorescent intensity increases as a function of boron acid concentration. This illustrates the fact that the presence of boron acid during the reaction influences the ratio of productive fluorescent product to nonproductive product(s). Thus in an assay stopped by conventional methods and not employing TCEP to enhance the effective working range of the, the inclusion of boron acid provides means for altering or eliminating the production of nonproductive product(s) with the attendant advantage that the critical point and in turn the working range of the assay can be increased. While Example IV illustrates the addition of boron acid from the use of boric acid, the boron acid can also be provided by the perborate ion, in the form of the salt, for example, sodium perborate. Accordingly, when the use of sodium perborate is used as the source of hydrogen peroxide, it can also have the advantageous effect of altering or eliminating the production of nonproductive product(s), thus increasing the effective working range of the assay.

What is claimed is:

1. In the method of assaying for peroxidase or peroxide activity comprising reacting a substrate solution containing a fluorogenic phenolic compound with peroxidase in the presence of hydrogen peroxide and measuring the resulting fluorescence intensity, the improvement comprising including in said assay, in an amount sufficient to enhance the effective working range of said assay, a boron acid or salt thereof, or a phosphine-based or hydride-based reducing agent.

2. The method of claim 1 wherein a metal chelating compound is present in the substrate solution.

3. The method of claim 2 wherein the boron acid is supplied in the form of boric acid, or salts thereof.

4. The method of claim 2 wherein the boron acid is supplied in the form of perborate, or salts therof.

5. The method of claim 2 wherein the reducing agent is selected from borohydride or tris(2-carboxylethyl) phosphine hydrochloride, or salts therof.

* * * * *